(12) United States Patent
Baldwin

(10) Patent No.: US 11,583,500 B2
(45) Date of Patent: Feb. 21, 2023

(54) SYSTEM FOR REMOTE ADMINISTERING OF MEDICAL CHEMICALS TO UNRESTRAINED ANIMALS

(71) Applicant: Benjamin Baldwin, Pollock Pines, CA (US)

(72) Inventor: Benjamin Baldwin, Pollock Pines, CA (US)

( * ) Notice: Subject to any disclaimer, the term of this patent is extended or adjusted under 35 U.S.C. 154(b) by 0 days.

(21) Appl. No.: 17/652,931

(22) Filed: Mar. 1, 2022

(65) Prior Publication Data
US 2022/0183985 A1 Jun. 16, 2022

Related U.S. Application Data

(63) Continuation-in-part of application No. 15/983,819, filed on Nov. 11, 2018, now abandoned.

(51) Int. Cl.
*A61K 9/20* (2006.01)
*A61M 37/00* (2006.01)
*A61K 9/00* (2006.01)
*F42B 12/54* (2006.01)

(52) U.S. Cl.
CPC .......... *A61K 9/2072* (2013.01); *A61K 9/0024* (2013.01); *A61M 37/0069* (2013.01); *F42B 12/54* (2013.01); *A61M 2250/00* (2013.01)

(58) Field of Classification Search
CPC ..... F42B 12/54; A61K 9/0024; A61K 9/2072; A61M 37/0069
USPC ....................................................... 102/512
See application file for complete search history.

(56) References Cited

U.S. PATENT DOCUMENTS

| | | | | |
|---|---|---|---|---|
| 4,326,524 A * | 4/1982 | Drake, Jr | ............. | A61K 9/0024 604/130 |
| 4,664,664 A * | 5/1987 | Drake, Jr. | ................. | A61D 7/00 102/512 |
| 5,648,637 A * | 7/1997 | Clark, III | .................. | F42B 5/03 102/491 |
| 6,375,971 B1 * | 4/2002 | Hansen | .................... | F42B 12/54 102/512 |
| 8,250,987 B1 * | 8/2012 | Morley | .................... | F42B 12/06 102/438 |
| 2006/0254453 A1 * | 11/2006 | Leal | ......................... | F42B 12/40 102/513 |
| 2007/0006769 A1 * | 1/2007 | Dodson | ..................... | F42B 6/10 102/508 |
| 2008/0196616 A1 * | 8/2008 | Cziglenyi | ............... | F42B 12/34 102/517 |
| 2012/0234198 A1 * | 9/2012 | Carmel | .................... | F42B 30/02 102/438 |

(Continued)

*Primary Examiner* — Bret Hayes
(74) *Attorney, Agent, or Firm* — Savantek Patent Services; Ivan E. Rozek

(57) ABSTRACT

A pellet having a convex shaped front includes a plurality of radially disposed surface slots. The concave shaped rear portion has a matching number of surface ribs that can be frictionally attached to the convex portion's slots. The pellet is constructed of a combination of medical compounds along with appropriate binders and other compounds that are pressed together under high pressure to produce a rigid mass capable of being propelled at high speeds and to pierce the skin of an animal or person where the compounds can be dissolved when contacting the internal liquid portion of the animal or person. The pellet can be loaded and propelled by a standard air rifle, gun, or pistol.

5 Claims, 6 Drawing Sheets

(56) References Cited

U.S. PATENT DOCUMENTS

2013/0087063 A1\* 4/2013 Halter .................... F42B 12/46
                                                          102/501
2014/0261042 A1\* 9/2014 Imhoff .................... F42B 5/03
                                                          102/438

\* cited by examiner

SYSTEM FOR REMOTE ADMINISTERING OF MEDICAL CHEMICALS TO UNRESTRAINED ANIMALS

CROSS REFERENCE TO RELATED APPLICATIONS

This application is a continuation-in-part of the U.S. application Ser. No. 15/983,819 filed Nov. 11, 2018, the entire content of which is incorporated herein by reference for continuity of disclosure.

STATEMENT REGARDING FEDERALLY SPONSORED RESEARCH OR DEVELOPMENT

Not Applicable.

DESCRIPTION OF ATTACHED APPENDIX

Not Applicable.

BACKGROUND OF THE INVENTION

This invention relates generally to the field of administering medical chemicals, such as medical treatment, vaccines, tranquilizer, and other similar chemicals to soft tissue of unrestrained animals or sometimes in extreme cases humans.

Typical non-lethal remote delivery systems and methods capable of penetrating the skin of the targeted animal available to-date comprise a frangible projectile having a hollow tip containing a chemical encapsulated in a capsule, or a special projectile with an embedded syringe preloaded with the chemical. In some instances, a dart may be used to deliver the chemicals.

The remote delivery systems available to-date are also typically dangerous to the targeted animal, complicated, and expensive to manufacture.

The payload of remote delivery systems available to-date is typically not adaptable and cannot be configured in-situ, such as on a range, in a forest or similar situations.

BRIEF SUMMARY OF THE INSTANT INVENTION

In accordance with an embodiment of the instant remote medical chemicals delivery system, there is disclosed a pellet having convex shaped front portion and a concave shaped rear portion, said convex shaped front portion including a plurality of radially displaced surface slots, said concave shaped rear portion having a plurality of radially displaced surface ribs that match and can be frictionally attached to said convex portion's radially displaced slots, and said bullet shaped pellet being constructed of a combination of disrupting compounds along with appropriate binders and other compounds that may be required that are pressed together under high pressure to produce a rigid mass capable of being propelled at high speeds to pierce the skin of an animal, or a person, where the compounds can be dissolved when contacting the internal liquid portion of said animal or person, that can be delivered by discharging from an air rifle or pistol.

In accordance with another embodiment of the instant remote medical chemicals delivery system, there is disclosed a pellet configured of a plurality of linearly stacked bullet shaped pellets enabling field configuration of the payload enabling adapting the payload to the requirements of the situation at the time of usage.

The features and advantages of described in this brief summary are not to be interpreted as all-inclusive. Additional features and advantages will be apparent to a person of ordinary skills in the art in view of the specification, drawings and claims provided in the instant application.

BRIEF DESCRIPTION OF THE DRAWINGS

The drawings constitute a part of this specification and include exemplary embodiments to the instant invention, which may be embodied in various forms. It is to be understood that in some instances various aspects of the instant embodiments may be shown exaggerated or enlarged to facilitate an understanding of the invention.

DETAILED DESCRIPTION OF THE PREFERRED EMBODIMENTS

Detailed descriptions of the preferred embodiment are provided herein. It is to be understood, however, that the present invention may be embodied in various forms. Therefore, specific details disclosed herein are not to be interpreted as limiting, but rather as a basis for the claims and as a representative basis for teaching one skilled in the art to employ the present invention in virtually any appropriately detailed system, structure or manner.

Figure 1:
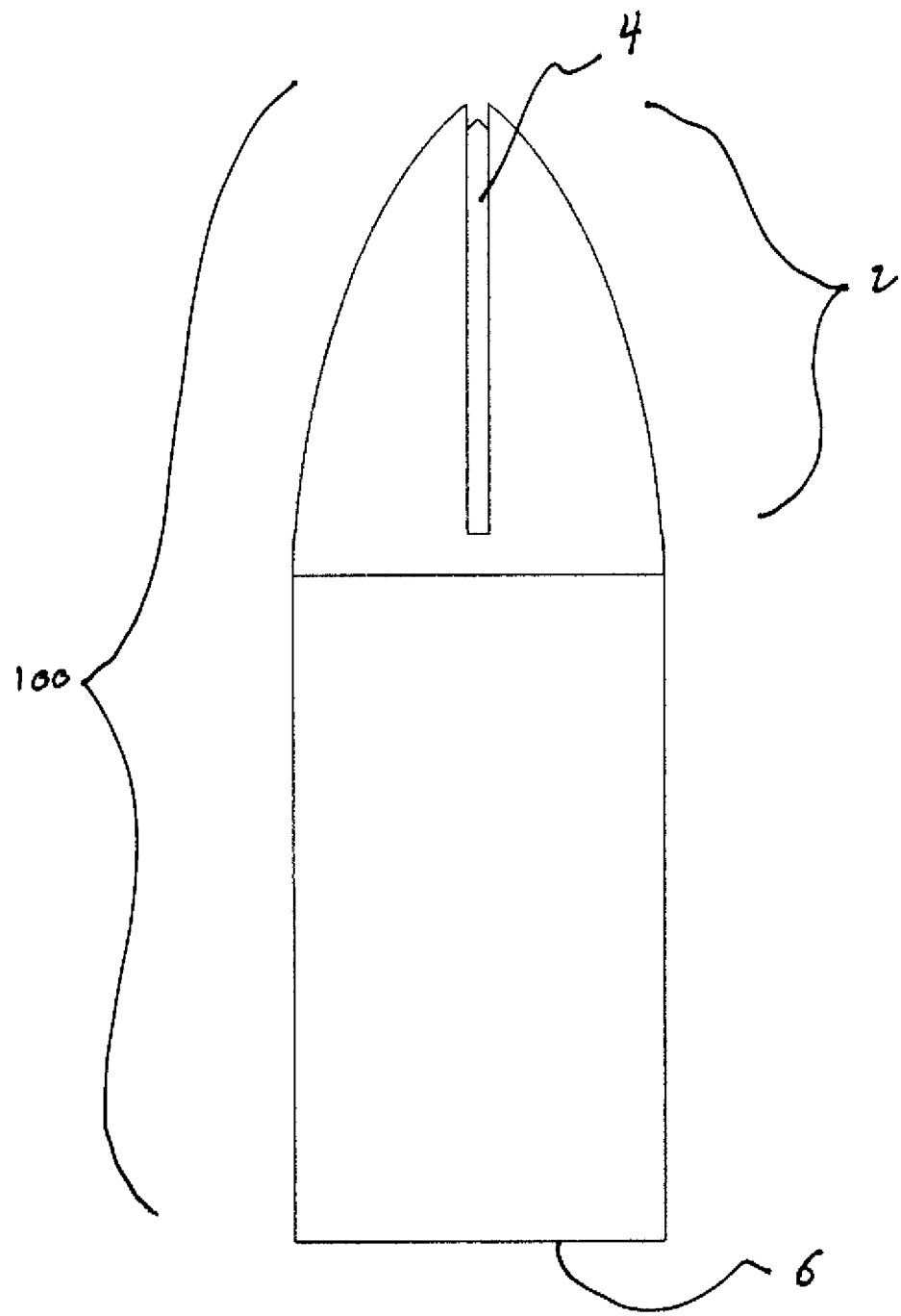
FIG. 1 front view of the invention.
Figure 2:
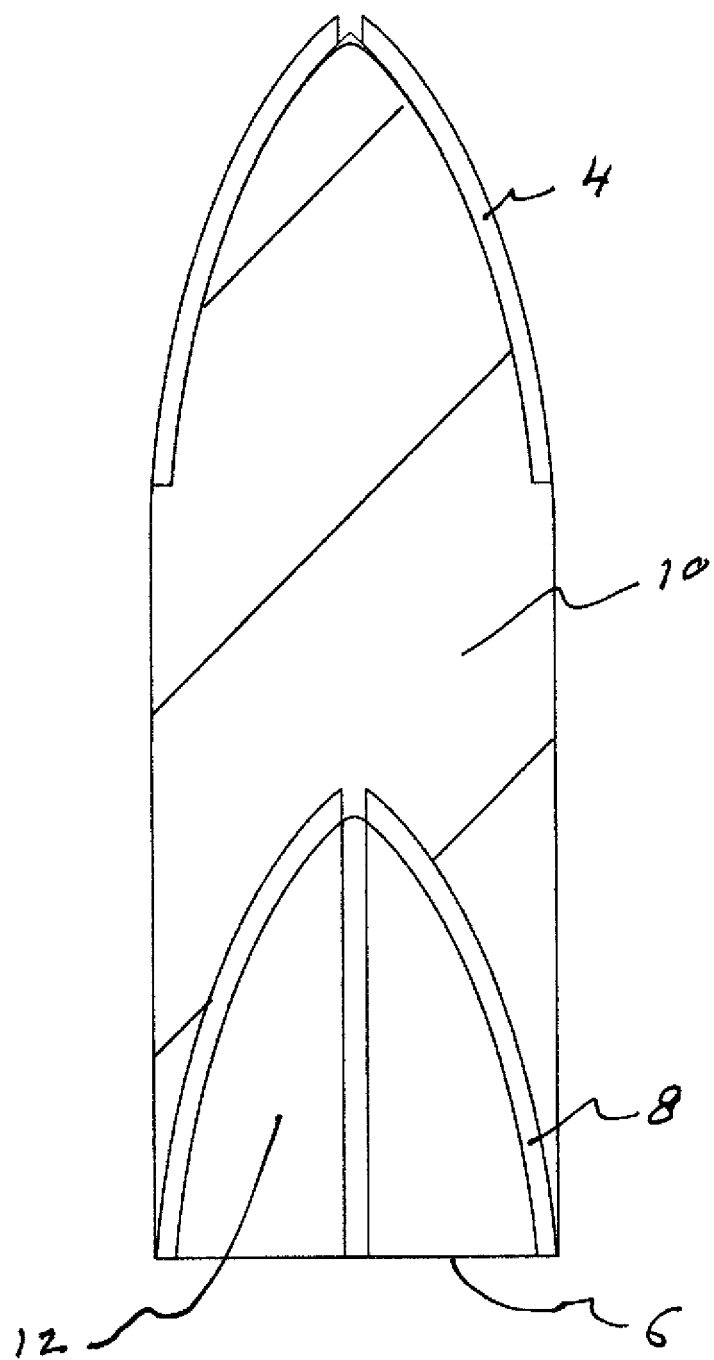
FIG. 2 is a front section view of the invention.
Figure 5:
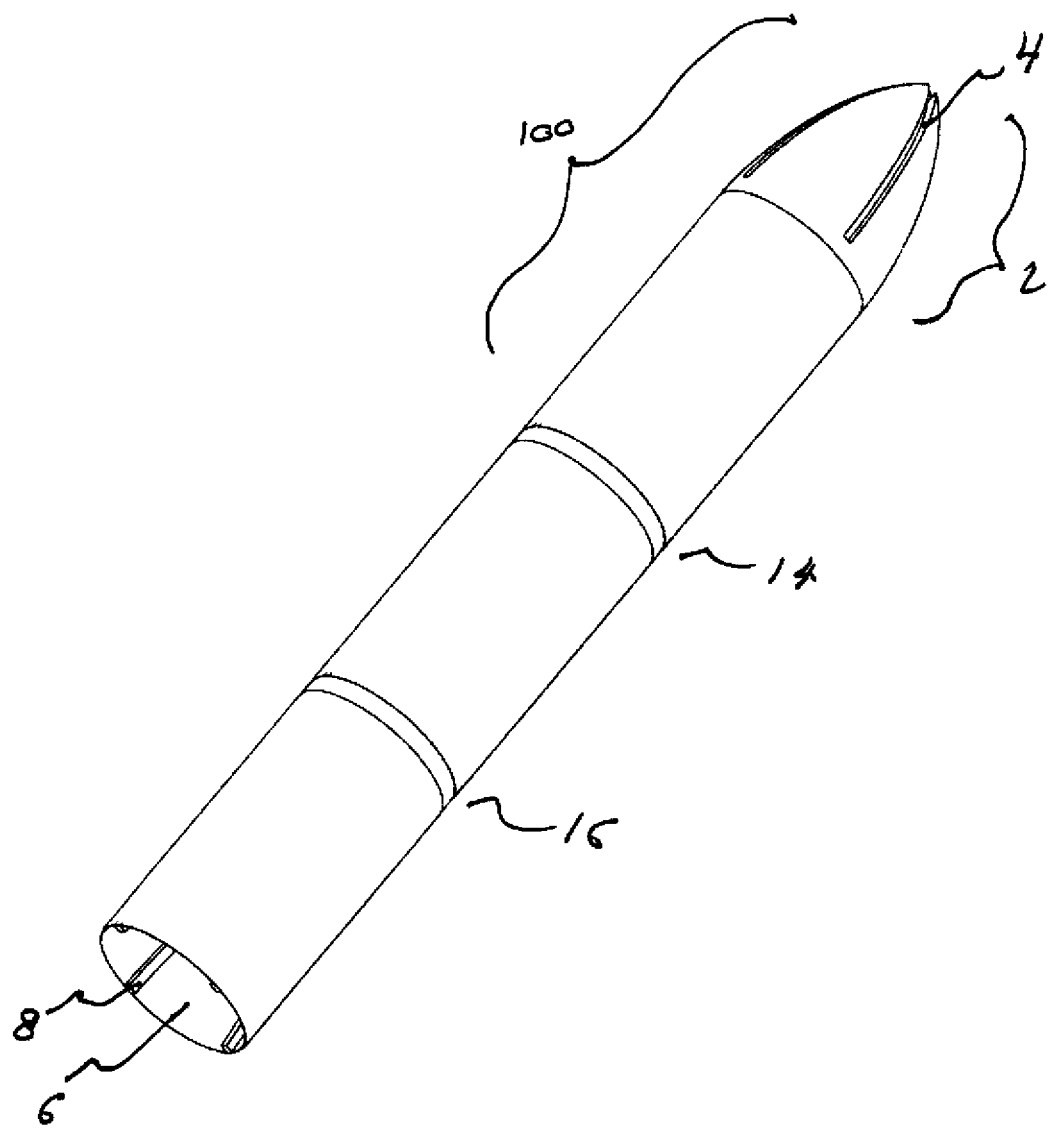
FIG. 5 is a perspective view of a plurality of pellets linearly attached to each other.
Figure 6:
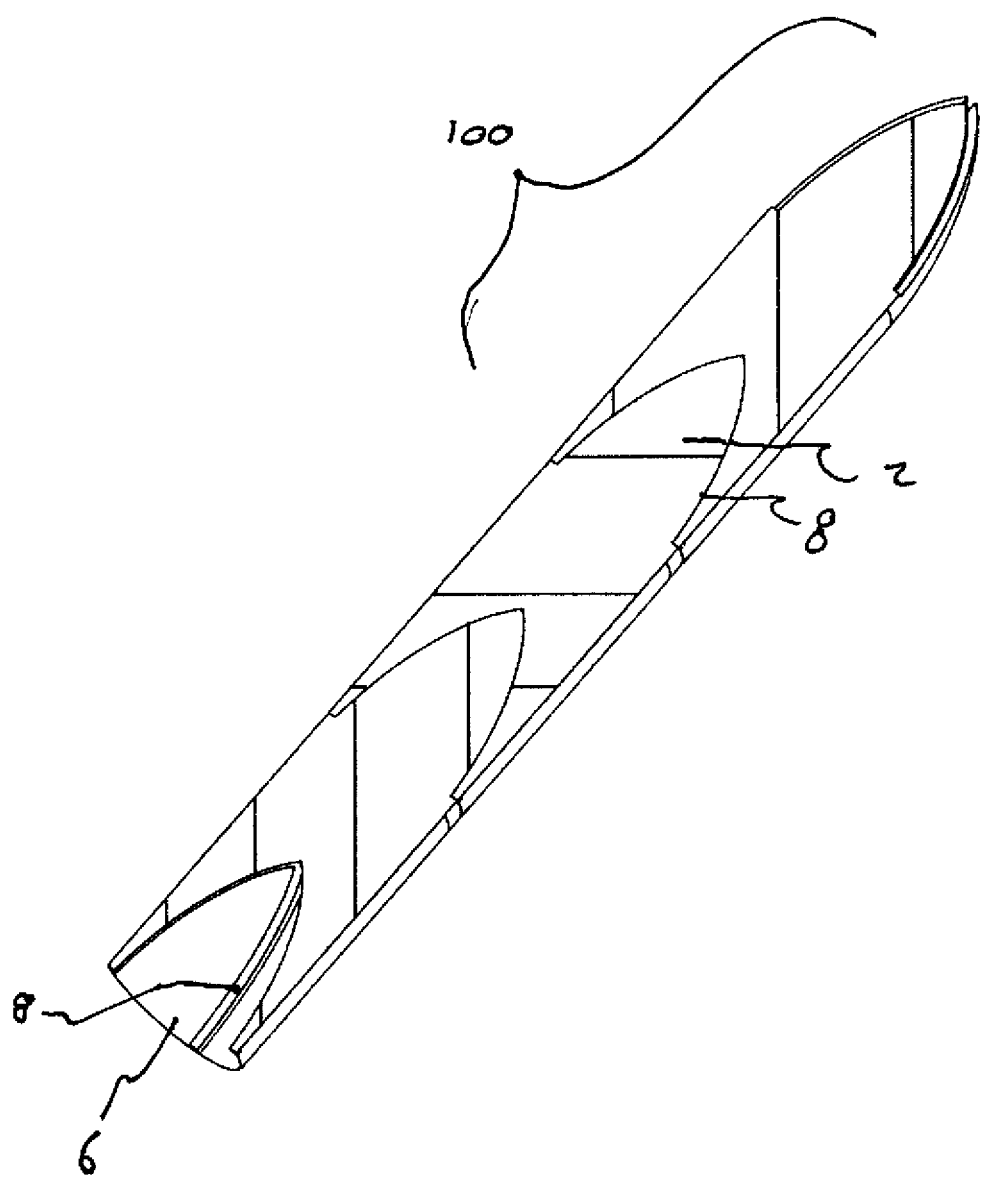
FIG. 6 is a side section view of a plurality of pellets linearly attached to each other.

Referring now to FIG. 1 we see a front view of the pellet 100. The pellet 100 is approximately bullet shaped and includes a convex tip 2 and a concave bottom 12, 6 as shown in FIG. 2. The convex portion 2 includes a number of radially disposed slots 4. Ribs 8 shown in FIG. 2 can frictionally engage the slots 4 allowing multiple pellets 100 to be linearly attached as shown in FIGS. 5 and 6. The number of slots 4 and the number of ribs 8 is identical as is the radial spacing.

Each pellet 100 is composed of chemical compounds that are compressed within a mold under high pressure to create the resulting bullet shape 100. The pressing and forming operation are similar to that of making traditional pills that are currently used in all types of pharmacological products as a means to orally ingest drug related compounds. In the case of the pellets 100 of the present invention, the pellet is propelled by a standard air rifle, gun, or pistol. The pellet 100 enters under the skin of the targeted animal or person and in doing so, comes into contact with the target's body liquids in the form of blood or other fluids which act to break down the pellet to allow the chemical ingredients of the pellet to enter the blood stream of the animal or person.

FIG. 2 is a section view that bisects the pellet 100. The recessed slots 4 at the upper tip of the pellet can engage with the ribs 8 shown at the bottom end 6 of the pellet 100 to create a multistage projectile as shown in FIGS. 5 and 6. The diameter, that is the caliber, of each pellet 100 is determined by the ordnance to be used to propel the pellet, preferably one of the following calibers: 0.177, 0.2, 0.22, 0.25, and 0.35. The length is variable, determined by the quantity of chemical compounds to be compressed within the pellet 100, most of the compressed material being in the solid cylindrical midsection 10 and the convex tip 2.

Figure 3:
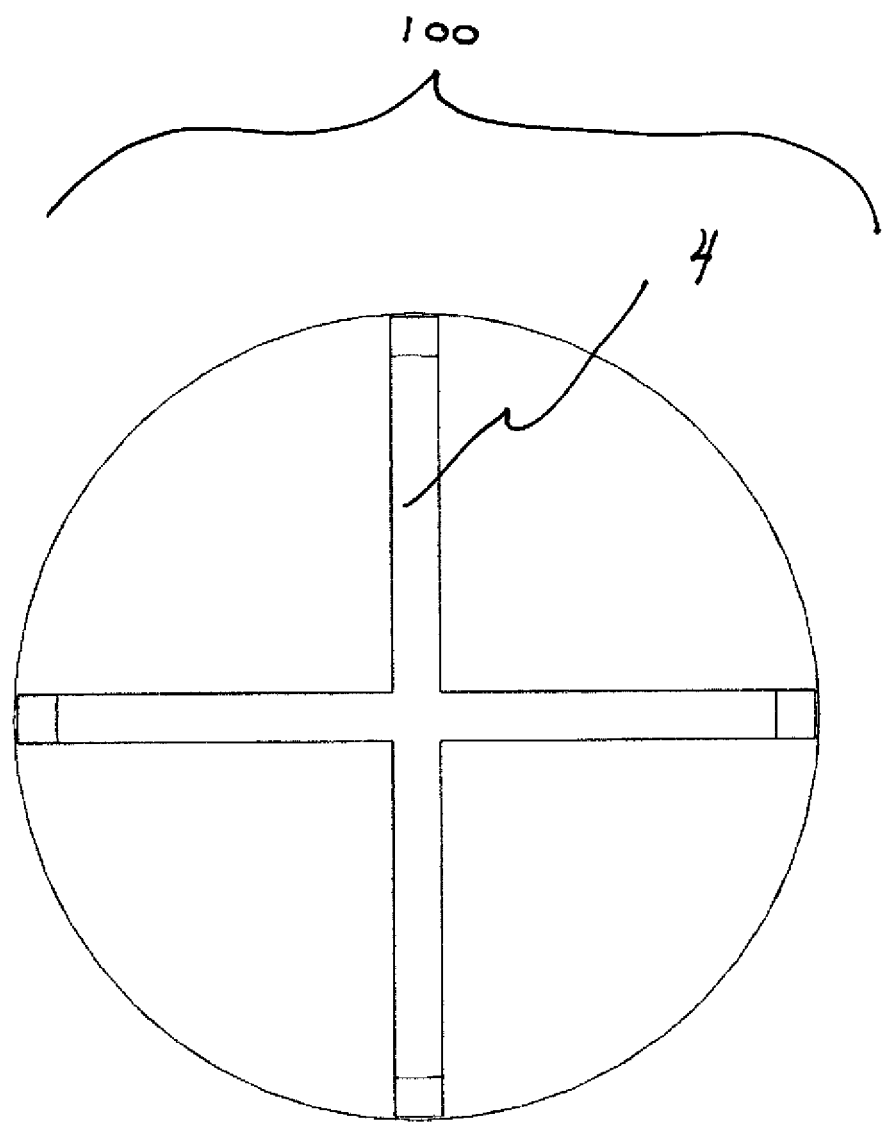
FIG. 3 is a top view of the invention.

FIG. 3 is a top view of the pellet 100 clearly showing the grooves 4.

Figure 4:
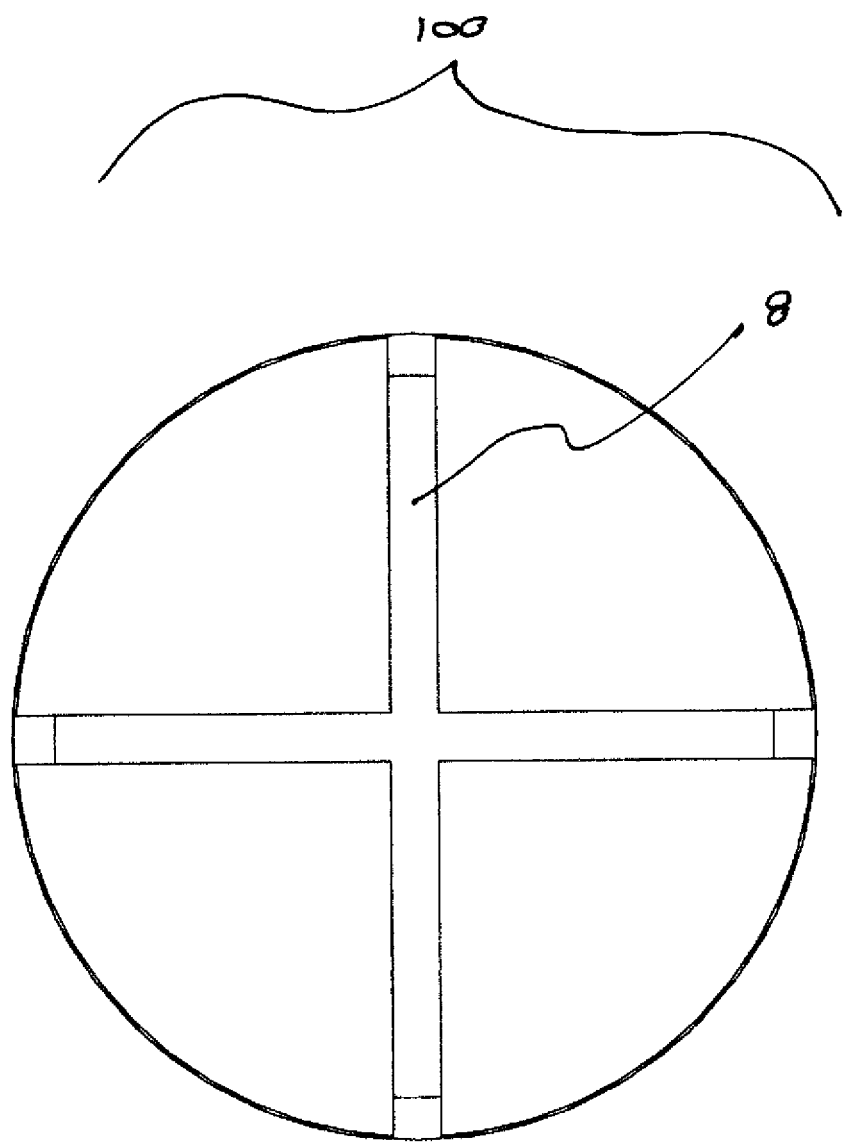
FIG. 4 is a bottom view of the invention.

FIG. 4 is a bottom view of the invention clearly showing the ribs 8 that can frictionally engage grooves 4 as shown in the section view in FIG. 6.

FIG. 5 is a perspective view of the pellet 100 showing multiple pellets linearly attached to each other so that they can be propelled as a group to be impaled into an animal or person's skin. In this case, each pellet 100 may have different chemical compounds to produce a variety of desired effects.

FIG. 6 is a section view that bisects three pellets 100. The frictional engagement of slots 4 and ribs 8 can be clearly seen.

Pellets disclosed in the preferred embodiments herein are designed for discharge from a conventional off the shelf air rifle or pistol. An alternate title for these pellets is Medicated Air Gun Implant Compounds (MAGIC). The MAGIC pellets comprise a new innovation in delivering therapeutic or immobilizing drugs to animals with possible applications to humans in military or law enforcement. These MAGIC pellets are coded using color code and/or a symbol to indicate the active ingredient of each pellet and to enable the user to combine chemicals for the efficient dose. They are stackable to adjust the amount of dosage of each tranquilizing chemical or compound. The rate of dissolution after skin penetration is controlled by the incorporation of disrupting compounds along with the appropriate binders and other chemicals. The disrupting compounds, binders and other chemicals are infused in each color-coded pellet for effective use and dosage.

In the claims, the word 'comprising' does not exclude the presence of other elements or steps then those listed in a claim. Furthermore, the terms "a" or "an," as used herein, are defined as "one, or more than one." Also, the use of introductory phrases such as "at least one" and "one or more" in the claims should not be construed to imply that the introduction of another claim element by the indefinite articles "a" or "an" limits any particular claim containing such introduced claim element to inventions containing only one such element, even when the same claim includes the introductory phrases "one or more" or "at least one" and indefinite articles such as "a" or "an." The same holds true for the use of definite articles. Unless stated otherwise, terms such as "first" and "second" are arbitrarily used to distinguish between the elements such terms describe. Thus, these terms are not necessarily intended to indicate temporal or other prioritization of such elements. The mere fact that certain measures are recited in mutually different claims does not indicate that a combination of these measures cannot be used to advantage.

What is claimed is:

1. A remote medical chemical delivery system for administering a plurality of chemicals to an animal or a human over distance, comprising:
   (a) at least one bullet shaped pellet comprising a convex shaped front portion, an elongate solid cylindrical midsection, and a concave shaped rear portion;
   (b) the bullet shaped pellet comprising rigid walls, the rigid walls comprised of the plurality of chemicals to be delivered to an animal or a human;
   (c) the convex shaped front portion comprising a plurality of radially evenly distributed slots;
   (d) the concave shaped rear portion comprising a plurality of radially evenly distributed ribs, wherein furthermore the plurality of ribs is the same as the plurality of radially evenly distributed slots of the convex shaped front portion;
   (e) the convex shaped front portion and the concave shaped rear portion having spatial dimensions complementing each other, the convex shaped front portion being able to frictionally engage the concave rear portion of another bullet shaped pellet creating a bullet shaped multistage projectile, the bullet shaped multistage projectile comprising the plurality of chemicals to be delivered to an animal or a human; and
   (f) the bullet shaped multistage projectile for delivering a plurality of chemicals to an animal or a human over distance to be propelled by a delivery ordnance to an animal or a human.

2. The remote medical chemical delivery system of claim 1, wherein each pellet is comprised of uniformly distributed compounds that dissolve subcutaneously or that dissolve intra-muscularly when contacting internal liquids of an animal or a human, said compounds being comprised of:
   at least one active ingredient;
   a combination of disrupting compounds;
   a combination of binders; and
   a combination of disinfecting compounds to protect small wound made by the bullet shaped multistage projectile cartridge.

3. The remote medical chemical delivery system of claim 1, wherein an amount of chemicals delivered to an animal or a human is controlled by spatial dimensions and number of individual pellets comprising the bullet shaped multistage projectile.

4. The remote medical chemical delivery system of claim 2, wherein the exterior surface of each pellet is coded according to the uniformly distributed compounds comprising the rigid walls of the individual pellet, the code being a color code, a symbol, or a combination of the color code and of the special symbol.

5. The remote medical chemical delivery system of claim 1, wherein the bullet shaped multistage projectile caliber is selected from the group comprising: 0.177, 0.2, 0.22, 0.25, and 0.35, corresponding to caliber of delivery ordnance.

* * * * *